(12) United States Patent
Olson

(10) Patent No.: US 11,607,497 B2
(45) Date of Patent: *Mar. 21, 2023

(54) MEDICAMENT DELIVERY DEVICE

(71) Applicant: SHL MEDICAL AG, Zug (CH)

(72) Inventor: Stephan Olson, Danderyd (SE)

(73) Assignee: SHL MEDICAL AG, Zug (CH)

( * ) Notice: Subject to any disclaimer, the term of this patent is extended or adjusted under 35 U.S.C. 154(b) by 22 days.

This patent is subject to a terminal disclaimer.

(21) Appl. No.: 17/374,642

(22) Filed: Jul. 13, 2021

(65) Prior Publication Data

US 2021/0338935 A1    Nov. 4, 2021

Related U.S. Application Data

(63) Continuation of application No. 15/036,295, filed as application No. PCT/EP2014/073527 on Nov. 3, 2014, now Pat. No. 11,129,939.

(51) Int. Cl.
| | |
|---|---|
| *A61M 5/24* | (2006.01) |
| *A61M 5/20* | (2006.01) |
| *A61M 5/315* | (2006.01) |
| *A61M 5/32* | (2006.01) |
| *A61M 11/00* | (2006.01) |

(52) U.S. Cl.
CPC ........ *A61M 5/2448* (2013.01); *A61M 5/2033* (2013.01); *A61M 5/2066* (2013.01);
(Continued)

(58) Field of Classification Search
CPC .............. A61M 5/2448; A61M 5/2033; A61M 5/2066; A61M 5/31583; A61M 5/31;
(Continued)

(56) References Cited

U.S. PATENT DOCUMENTS

| | | |
|---|---|---|
| 5,320,609 A | 6/1994 | Haber et al. |
| 5,480,387 A | 1/1996 | Gabriel et al. |
| (Continued) | | |

FOREIGN PATENT DOCUMENTS

| | | |
|---|---|---|
| WO | 2010/000559 A1 | 1/2010 |
| WO | 2012/067583 A1 | 5/2012 |
| (Continued) | | |

OTHER PUBLICATIONS

EPO, Int'l Search Report in PCT/EP2014/073527, dated Feb. 27, 2015.

*Primary Examiner* — Joseph D. Boecker
*Assistant Examiner* — Brian T Khong
(74) *Attorney, Agent, or Firm* — McDonnell Boehnen Hulbert & Berghoff LLP

(57) ABSTRACT

A medicament delivery device includes a housing having a longitudinal axis, a container holder, an axially movable plunger adapted to be displaced along the longitudinal axis into the container holder, and an energy accumulating member arranged inside the housing and adapted for displacing the plunger along the longitudinal axis. The plunger includes an outer plunger rod and an inner plunger rod arranged at least partially inside the outer plunger rod, the inner plunger rod being threadedly engaged with the outer plunger rod and manually rotatable to displace the inner plunger rod along the longitudinal axis into the container holder.

20 Claims, 3 Drawing Sheets

(52) U.S. Cl.
CPC ...... *A61M 5/31583* (2013.01); *A61M 11/007* (2014.02); *A61M 2005/2451* (2013.01); *A61M 2005/31518* (2013.01); *A61M 2005/3267* (2013.01)

(58) Field of Classification Search
CPC .......... A61M 5/31578; A61M 5/31553; A61M 5/31586; A61M 5/31593; A61M 5/3156; A61M 5/31535; A61M 5/31556; A61M 5/31575; A61M 5/315; A61M 5/24; A61M 5/31541; A61M 5/3155; A61M 5/20; A61M 2005/2451; A61M 2005/2488; A61M 2005/31518; A61M 2005/3267; A61M 2005/31598; A61M 2005/2013; A61M 2005/202; A61M 11/007; A61M 11/08; A61M 15/00; A61M 35/00; A61F 9/00
See application file for complete search history.

(56) References Cited

U.S. PATENT DOCUMENTS

| | | | |
|---|---|---|---|
| 8,617,124 B2 | 12/2013 | Wieselblad et al. | |
| 8,926,558 B2 | 1/2015 | Ratjen et al. | |
| 9,011,386 B2 | 4/2015 | Kronestedt et al. | |
| 9,283,325 B2 | 3/2016 | Karlsson | |
| 9,649,446 B2 | 5/2017 | Wieselblad | |
| 9,937,297 B2 | 4/2018 | Bergens | |
| 2006/0276753 A1* | 12/2006 | Kronestedt | A61M 15/0065 604/186 |
| 2010/0065049 A1* | 3/2010 | Farieta | A61M 11/08 604/82 |
| 2011/0054412 A1 | 3/2011 | Eich et al. | |
| 2012/0029443 A1 | 2/2012 | Holmqvist | |
| 2012/0041366 A1 | 2/2012 | Fayyaz et al. | |
| 2012/0136315 A1* | 5/2012 | Wieselblad | A61M 5/2448 604/189 |
| 2012/0165752 A1 | 6/2012 | Holmqvist et al. | |
| 2013/0102971 A1 | 4/2013 | Olson | |
| 2015/0151053 A1 | 6/2015 | Holmqvist | |
| 2015/0250953 A1 | 9/2015 | Elmen | |
| 2016/0235924 A1 | 8/2016 | Soerensen et al. | |

FOREIGN PATENT DOCUMENTS

| | | |
|---|---|---|
| WO | 2012/085208 A1 | 6/2012 |
| WO | 2012/173553 A1 | 12/2012 |

* cited by examiner

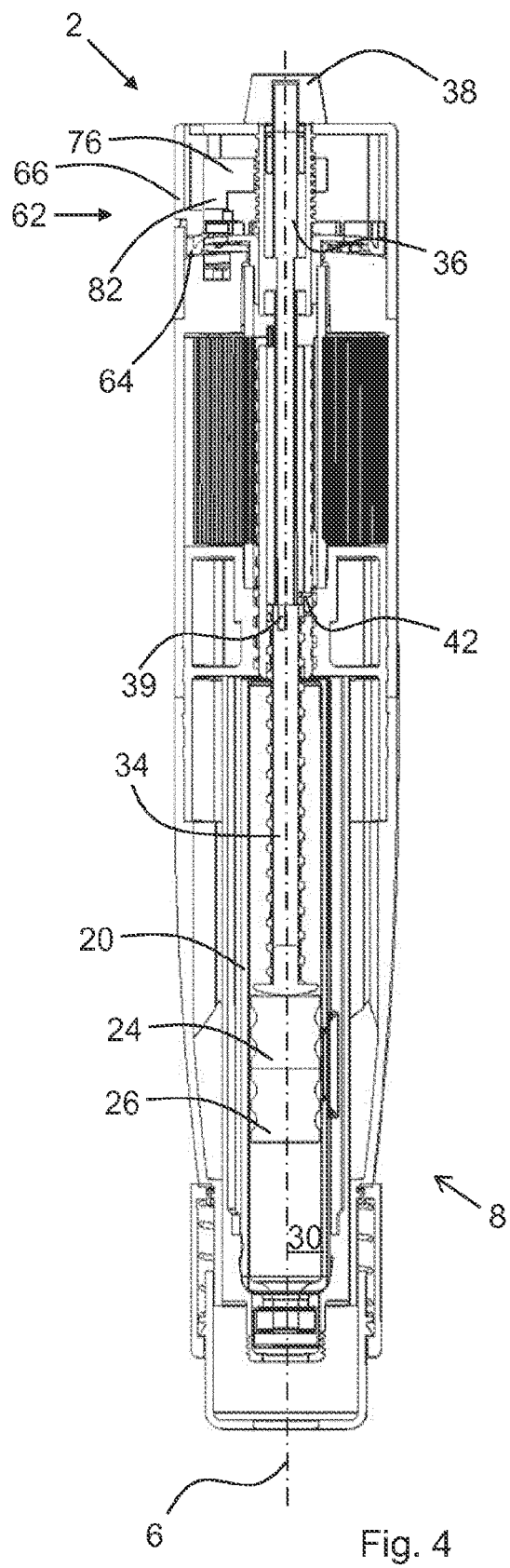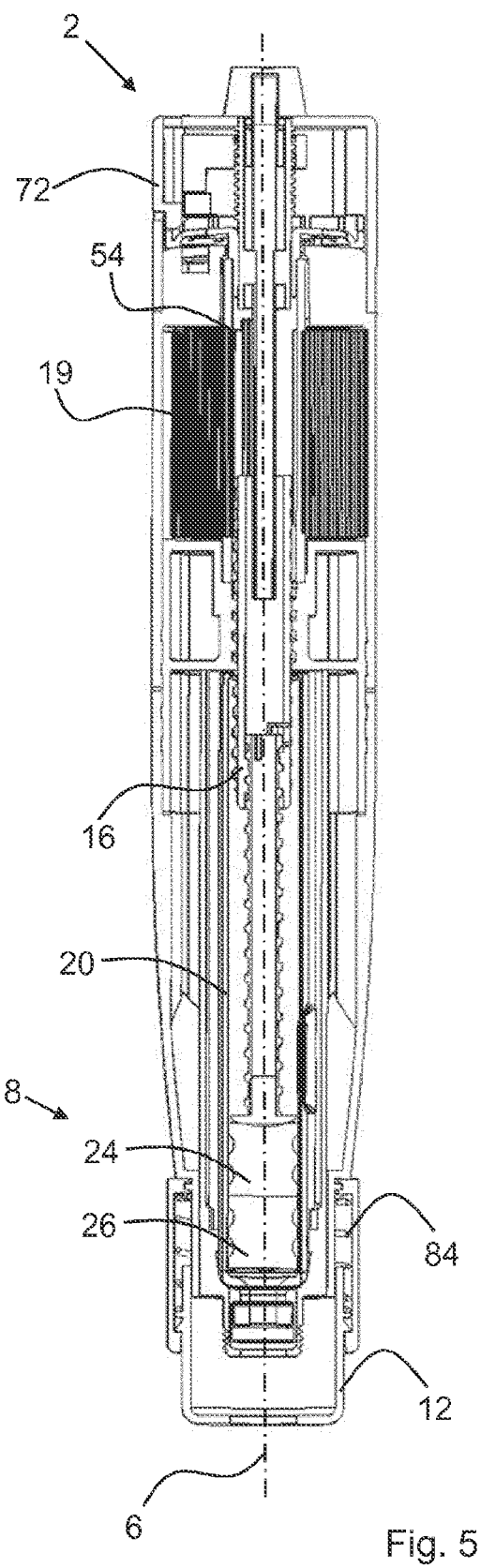

MEDICAMENT DELIVERY DEVICE

CROSS REFERENCE TO RELATED APPLICATIONS

The present application is a continuation of U.S. patent application Ser. No. 15/036,295, filed May 12, 2016, which is a U.S. National Phase Application pursuant to 35 U.S.C. § 371 of International Application No. PCT/EP2014/073527 filed Nov. 3, 2014, which claims priority to Swedish Patent Application No. 1351351-0 filed Nov. 15, 2013. The entire disclosure contents of these applications are herewith incorporated by reference into the present application.

TECHNICAL FIELD

Embodiments disclosed herein relate to medicament delivery devices for the administering of medicaments, in particular medicament delivery devices providing a mixing of two medicament components, such as a liquid and a powder, or two liquids.

BACKGROUND

The present invention relates to medicament delivery devices such as automatic injection devices for injecting liquid medicament with a needle in a patient, or nebulisers for administering a medicament in the form of a mist to be inhaled into the lungs of a patient.

Auto-injectors, or pen-injectors have been on the market for many years. During recent years some medicaments have been developed to be injected by patients themselves. Therefore, depending on the intended use and type of medicament, there have also been developed injection devices having a varying degree of automatic functions to facilitate the injection of medicaments in a reliable and safe way for patients and even for trained personnel; e.g. physicians and nurses.

WO 2012/173553 discloses an injection device comprising a housing and a container holder arranged within the housing. The container holder is configured for accommodating a medicament container having a needle attached to one end thereof and a stopper sealingly and slidably arranged inside the medicament container at the other end thereof. A plunger rod is arranged with a proximal end thereof contactable with the stopper. A first and a second energy accumulating member is arranged in the interior of the housing of the injection device and adapted to accumulate and store energy. A plunger drive means is slidably arranged in relation to the plunger rod, is rotationally locked to the plunger rod, and is rotatable in relation to the housing. The plunger drive means is operationally associated with the first energy accumulating member. A container driver is arranged for being connectable to the container holder and is threadedly connected to the plunger rod. The container driver is operationally associated with the second energy accumulating member such that due to an output axial force from the second energy accumulating member, the container holder and the plunger rod are axially moveable in relation to the housing along a predetermined distance towards the proximal end of the injection device from an initial locked position to a second position whereby a needle penetration is performed. The plunger drive means is locked from being rotated by the container driver. The plunger drive means is released such that due to an output torque from the first energy accumulating member, the plunger drive means is allowed to be rotated and the plunger rod is urged towards the proximal end of the injection device whereby an injection is performed.

Some medicaments which are administered via medicament delivery devices comprise two medicament components, which require mixing before being administered via a relevant medicament delivery device such as an injection device or a nebuliser.

In the context of a piston rod drive system for a manually operable drug delivery device, WO 2012/085208 discloses a piston rod drive system comprising a main body adapted for coupling with a reservoir. A user operable activation element is operatively coupled with the main body and configured to move axially and rotationally relative to the main body between a first position and a second position to transfer a solvent from a rear chamber of a cartridge to a front chamber thereof. A piston rod element is operatively coupled with the activation element and the main body and configured to move axially and non-rotationally relative to the main body in response to the activation element being moved between the first position and the second position. The drug delivery device as such does not lend itself to be automated.

There exists a need for a medicament delivery device, which provides for a mixing of two medicament components and an automatic delivery of the mixed components.

SUMMARY

It is an objective to provide an automatic medicament delivery device, which provides for a mixing of two medicament components held in a medicament container.

According to an aspect, this is achieved by a medicament delivery device comprising:

a housing having a longitudinal axis extending between, and along, a proximal end portion and a distal end portion of the housing, a container holder arranged in the housing at the proximal end portion, an axially movable plunger adapted to be displaced along the longitudinal axis into the container holder, and an energy accumulating member arranged inside the housing, the energy accumulating member being adapted for displacing the plunger along the longitudinal axis towards the proximal end portion. The container holder is adapted to accommodate a medicament container adapted for attachment of a medicament delivery member at one end portion of the medicament container and comprises a first piston sealingly and slidably arranged inside an opposite end portion of the medicament container, and a second piston slidably arranged inside an intermediate portion of the medicament container. The plunger comprises an outer plunger rod, and an inner plunger rod arranged at least partially inside the outer plunger rod. The inner plunger rod is arranged in threaded engagement with the outer plunger rod. The inner plunger rod is manually rotatable to displace the inner plunger rod along the longitudinal axis in a direction towards the proximal end portion into the container holder.

Since the inner plunger rod is arranged in threaded engagement with the outer plunger rod and the inner plunger rod is manually rotatable to displace the inner plunger rod along the longitudinal axis in a direction towards the proximal end portion into the container holder, the inner plunger rod is adapted to displace the first piston and a mixing of two medicament components in a relevant medicament container held in the container holder is achieved. As a result, the above mentioned objective is achieved.

The medicament delivery devices may be, for instance, be an injection device for injecting medicament in fluid form, or a nebuliser for administering a medicament in the form of a mist to be inhaled into the lungs. The medicament is at least partially administered and powered by the energy accumulating member displacing the plunger. The medicament delivery member may comprise a needle as used in an injection device, or a nozzle as used in a nebuliser.

According to embodiments, the medicament delivery device may comprise an actuation rod extending at least partially inside the inner plunger rod. The actuation rod may be arranged in sliding engagement with the inner plunger rod, such that upon rotation of the actuation rod, the inner plunger rod may be rotated and slid along the longitudinal axis. Thus, the inner plunger rod, due to the threaded engagement with the outer plunger rod, may slide along the actuation rod, and the inner plunger rod may be displaced into the container holder upon rotation of the actuation rod.

According to embodiments, the actuation rod may comprise a knob arranged outside the housing at the distal end portion. In this manner, a user may easily rotate the actuation rod by turning the knob.

According to embodiments, the actuation rod may be adapted to lose its sliding engagement with the inner plunger rod when the inner plunger rod is positioned in an end position towards the proximal end portion in the outer plunger rod. In this manner, displacement of the inner plunger rod may stop when the inner plunger rod reaches the end position, even if a user should continue to rotate the actuation rod.

According to embodiments, the outer plunger rod may be adapted to engage with the inner plunger rod when the inner plunger rod is positioned in an end position towards the proximal end portion. In this manner, it may be ensured that the inner plunger rod remains in a position towards the proximal end portion when the entire plunger is to be displaced towards the proximal end portion to administer a medicament from a relevant medicament container in the container holder.

According to embodiments, the outer plunger rod may comprise at least one resilient projection adapted to engage with a recess in the inner plunger rod when the inner plunger rod is positioned in the end position towards the proximal end portion. In this manner, the outer plunger rod may engage with the inner plunger rod.

According to embodiments, the energy accumulating member may comprise a torsion spring for transferring stored energy into a rotational movement for the displacement of the plunger along the longitudinal axis in a direction towards the proximal end portion. In this manner, a sufficient force for administering a medicament may be provided within a comparatively small space. The torsion spring may, for instance, extend around a portion of the plunger.

According to embodiments, the medicament delivery device may comprise a fixed member arranged inside the housing. The fixed member may be provided with a threaded inner surface, wherein the outer plunger rod may comprise a threaded outer surface. The threaded inner surface of the fixed member may engage with the threaded outer surface of the outer plunger rod. A first end of the torsion spring may be connected to the housing and a second end of the torsion spring may be connected to the outer plunger rod and may be releasably engaged with the housing. In this manner, the torque from the torsion spring may be transferred to the plunger rod. Moreover, energy may be stored in the torsion spring until the second end of the torsion spring is released from engagement with the housing.

According to embodiments, the outer plunger rod may be engaged with the second end of the torsion spring via a drive member. The outer plunger rod may be slidably connected with the drive member for sliding movement of the outer plunger rod along the drive member and the longitudinal axis. In this manner, the torque from the torsion spring may be transferred via the drive member to the plunger rod. The outer plunger rod will slide along the longitudinal direction at least partially inside the drive member while the drive member is rotated. The rotation of the outer plunger member will advance the entire plunger towards the proximal end portion as the threaded outer surface of the outer plunger rod is engaged with the threaded inner surface of the fixed member.

According to embodiment, the medicament delivery device may comprise a locking arrangement for releasably locking the torsion spring in an energy storing position. In this manner, the locking arrangement may be actuated to release the torsion spring.

According to embodiments, the locking arrangement may comprise a first member connected to the torsion spring and a second member connected to the housing, the second member being adapted to be in a releasable engagement with the first member. In his manner, a user may actuate the second member to release the first member in order to release the torsion spring.

According to embodiments, the locking arrangement may comprise a third member being threadedly connected with the actuation rod and slidably arranged in relation to the housing, wherein the third member in a blocking position may be arranged in abutment with the second member, and wherein a rotation of the actuation rod may slide the third member along the longitudinal axis and out of the abutment with the second member. In this manner, an unintentional actuation of the second member may be prevented before the mixing of two medicaments in a medicament container held in the container holder.

According to embodiments, the first member may comprise an opening and the third member may comprise a projection, the projection extending through the opening to achieve a releasable engagement between the third and first members. In this manner, an additional locking of the first member may be achieved.

According to embodiments, the rotation of the actuation rod may slide the third member along the longitudinal axis and release the releasable engagement with the first member.

Further features of embodiments and advantages will become apparent when studying the appended claims and the following detailed description.

BRIEF DESCRIPTION OF THE FIGURES

Various aspects of embodiments, including their particular features and advantages, will be readily understood from the example embodiments discussed in the following detailed description and the accompanying drawings, in which:

FIG. 4 illustrates a cross section through the embodiments of the medicament delivery device of FIGS. 1-3, and FIG. 5 illustrates a cross section through the embodiments of the medicament delivery device of FIGS. 1-4.

DETAILED DESCRIPTION

Aspects of example embodiments will now be described more fully. Like numbers refer to like elements throughout. Well-known functions or constructions will not necessarily be described in detail for brevity and/or clarity.

Figure 1:
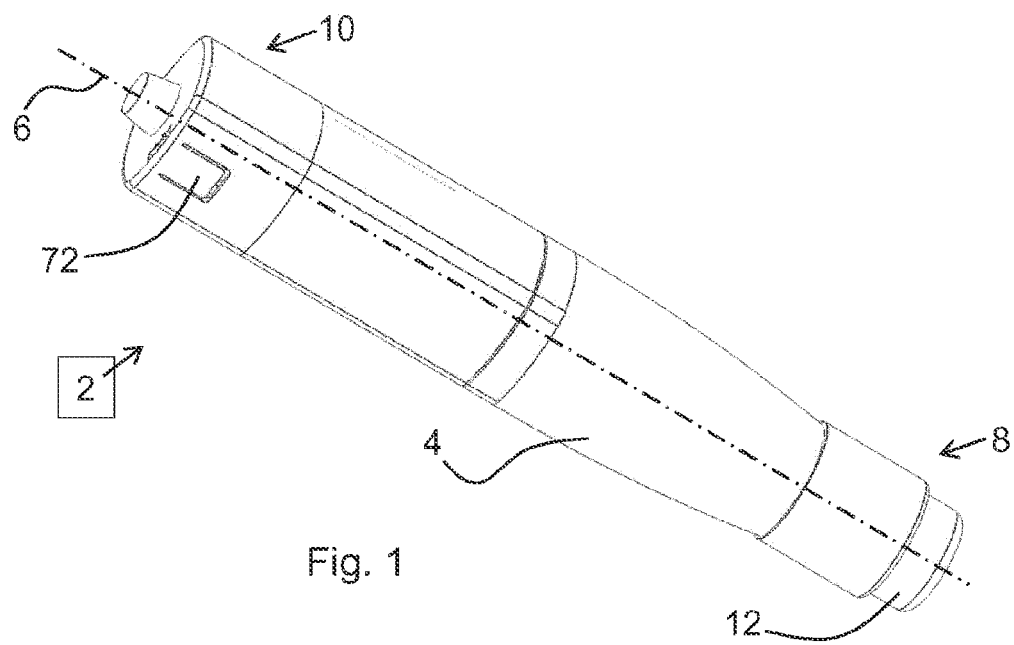
FIG. 1 illustrates a medicament delivery device according to embodiments.

FIG. 1 illustrates a medicament delivery device 2 according to embodiments. In these embodiments, the medicament delivery device 2 is illustrated in the form of auto injector. The medicament delivery device 2 comprises a housing 4 having a longitudinal axis 6 extending between, and along, a proximal end portion 8 and a distal end portion 10 of the housing 4. A medicament delivery member in the form of a needle assembly is arranged to be connected at the proximal end portion 8. A cover 12 is provided at the proximal end portion 8.

Figure 2:
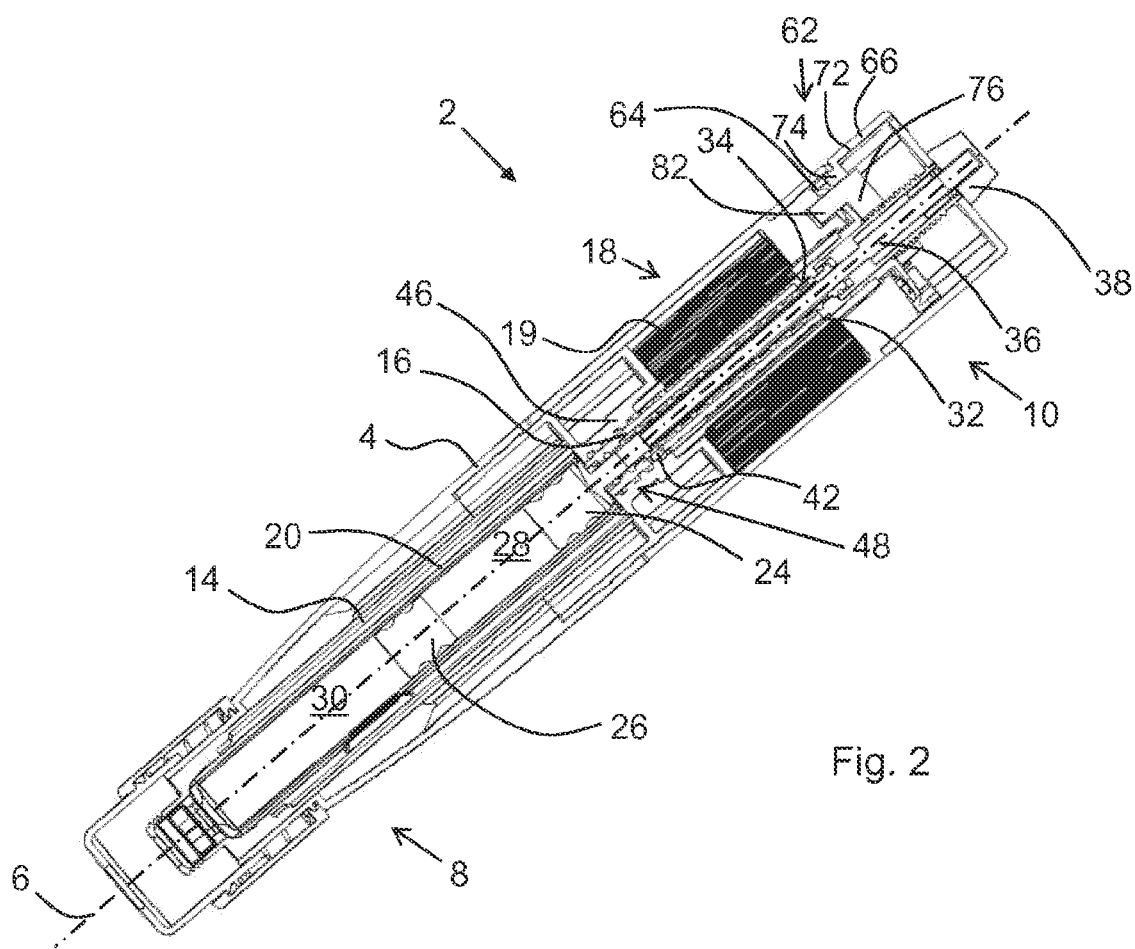
FIG. 2 illustrates a cross section through the medicament delivery device illustrated in FIG. 1.

FIG. 2 illustrates a cross section through the medicament delivery device 2 illustrated in FIG. 1. A container holder 14 is arranged in the housing 4 at the proximal end portion 8. An axially movable plunger 16 is adapted to be displaced along the longitudinal axis 6 into the container holder 14. An energy accumulating member 18 is arranged inside the housing 4.

The energy accumulating member 18 is adapted to displace the plunger 16 along the longitudinal axis 6 towards the proximal end portion 8. The energy accumulating member 18 comprises a torsion spring 19 for transferring stored energy into a rotational movement for the displacing of the plunger 16 along the longitudinal axis in a direction towards the proximal end portion 8. The displacement of the plunger 16 will be further discussed with reference to FIGS. 3-5 below.

The container holder 14 is adapted to accommodate a medicament container 20. The medicament container 20 is adapted for attachment of the medicament delivery member, comprising a needle at a first end portion of the medicament container 20 at the proximal end portion 8 of the housing 4. The medicament container 20 comprises a first piston 24 sealingly and slidably arranged inside an opposite end portion of the medicament container 20, and a second piston 26 slidably arranged inside an intermediate portion of the medicament container 20.

Such a medicament container 20 is adapted to contain two medicament components, one of which is stored in a first space 28 between the first piston 24 and the second piston 26. The other medicament component is stored in a second space 30 between the first end portion of the medicament container 20 and the second piston 26. The two medicament components require mixing before being administered to a patient.

The plunger 16 comprises an outer plunger rod 32 and an inner plunger rod 34 arranged at least partially inside the outer plunger rod 32. The inner plunger rod 34 is arranged in threaded engagement with the outer plunger rod 32. The inner plunger rod 34 is manually rotatable to displace the inner plunger rod 34 along the longitudinal axis 6 in a direction towards the proximal end portion 8 into the container holder 14 and the medicament container 20 to displace the first piston 24 towards the second piston 26. Thus, the medicament in the first space 28 is transferred into the second space 30. For instance, 8-14 full revolutions of the inner plunger rod 34 may be required for the inner plunger rod 34 to extend into the medicament container 20 to such an extent that the first piston 24 abuts against the second piston 26.

An actuation rod 36 extends inside the inner plunger rod 34. The actuation rod 36 is arranged in sliding engagement with the inner plunger rod 34, and it is via the actuation rod 36 that the inner plunger rod 34 is rotated. Accordingly, when the actuation rod 36 is rotated, the inner plunger rod 34 is rotated and due to the threaded engagement with the outer plunger rod 32, the inner plunger rod 34 is slid along the actuation rod 36 and the longitudinal axis 6. During rotation, the actuation rod 36 remains in the same position along the longitudinal axis 6. The actuation rod 36 comprises a knob 38 arranged outside the housing 4 at the distal end portion 10 for a user to grasp and rotate.

The medicament delivery device 2 comprises a locking arrangement 62 for releasably locking the torsion spring 19 in an energy storing position. The locking arrangement comprises a first member 64 connected to the torsion spring 19 and a second member 66 connected to the housing 4. The second member 66 is adapted to be in a releasable engagement with the first member 64. In these embodiments, the first member 64 comprises a disc 68 provided with peripheral radial slots 70, see FIG. 3. The second member 66 comprises a button 72 arranged in the housing 4, see also FIG. 1. The button 72 comprises at least one protruding member 74 adapted to fit into at least one of the radial slots 70.

Figure 3:
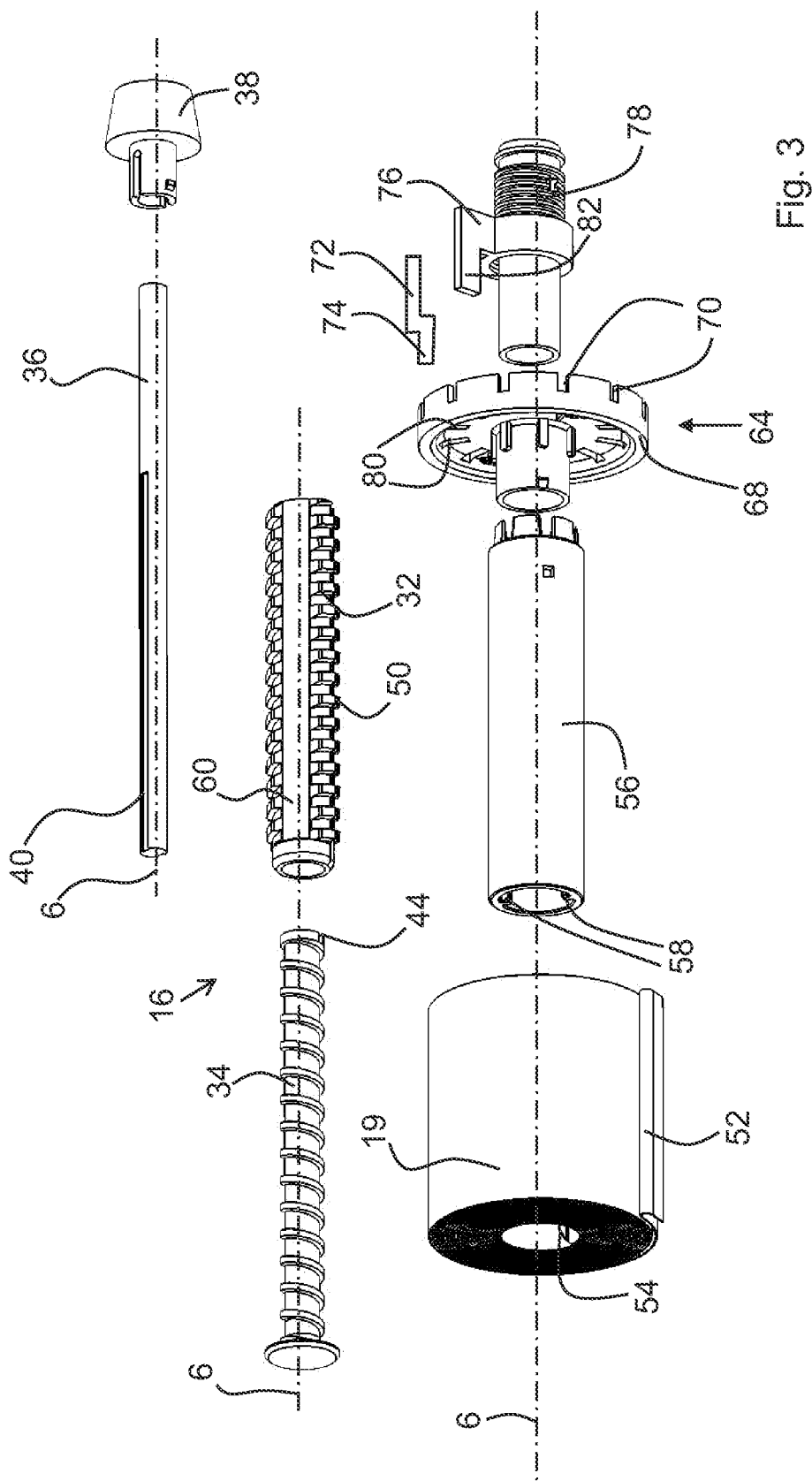
FIG. 3 illustrates parts of the medicament delivery device illustrated in FIGS. 1 and 2 in an exploded view.

FIG. 3 illustrates the plunger 16, the actuation rod 36, the energy accumulating member 18, and part of the locking arrangement of the FIGS. 1 and 2 embodiments in an exploded view.

The actuation rod 36 is provided with a slot 40 extending along the actuation rod 36. The inner plunger rod 34 on its inside is provided with a protrusion 39 (see FIG. 4), which extends into the slot 40. Thus, the sliding engagement between the actuation rod 36 and the inner plunger rod 34 is achieved. The knob 38 is fixedly attached to the actuation rod 36 to form one rotatable unit with the actuation rod 36.

The inner plunger rod 34 is adapted to engage with the outer plunger rod 32 when the inner plunger rod 34 is positioned in an end position towards the proximal end portion 8, see also FIG. 4. For this purpose, the outer plunger rod 32 comprises at least one resilient projection 42 (see FIGS. 2 and 4) adapted to engage with a recess 44 in the inner plunger rod 34 when the inner plunger rod 34 is positioned in the end position towards the proximal end portion 8.

In the following, reference is made to FIGS. 3 and 2. A fixed member 46 is arranged inside the housing 4. The fixed member 46 is provided with a threaded inner surface 48. The outer plunger rod 32 comprises a threaded outer surface 50. The threaded inner surface 48 engages with the threaded outer surface 50.

A first end 52 of the torsion spring 19 is connected to the housing 4 and a second end 54 of the torsion spring 19 is connected to the outer plunger rod 32. The second end 54 is furthermore releasably engaged with the housing 4. In these embodiments, the second end 54 is connected to the outer plunger rod 32 via a drive member 56. Accordingly, the outer plunger rod 32 engages with the second end 54 of the torsion spring 19 via the drive member 56. The outer plunger 32 is slidably connected with the drive member 56 for sliding movement of the outer plunger rod 32 along the drive member 56 and the longitudinal axis 6. Such a slidable connection may for instance be achieved by an inner side of the drive member 56 being provided with at least one ridge 58 extending along the longitudinal axis 6 and an outer side of the outer plunger rod 32 being provided with at least one ridge recess 60 extending along the longitudinal axis 6. The at least one ridge 58 fits slidably in the at least one ridge recess 60.

Thus, when the second end 54 of the torsion spring 19 is released, the stored energy from the torsion spring 19 is transferred as a torque via the drive member 56 to the outer plunger rod 32. The drive member 56 and the outer plunger rod 32 will be rotated by the torsion spring 19. While rotating, seen in a direction along the longitudinal axis 6, the drive member 56 remains stationary while the outer plunger rod 32, with its threaded outer surface 50 engaging with the threaded inner surface 48 of the fixed member 46, is moved towards the proximal end portion 8.

The first member 64, i.e. the disc 68 of the locking arrangement is connected to the second end 54 of the torsion spring 19 via the drive member 56. Thus, as long as the disc 68 is locked by the at least one protruding member 74 of the button 72 engaging with at least one of the slots 70, the torsion spring 19 remains in its energy storing position. Only upon actuation of the button 72, the disc 68 and the torsion spring 19 are released.

The locking arrangement comprises a third member 76 being threadedly connected with the actuation rod 36 and slidably arranged in relation to the housing. The third member 76 is connected with the actuation rod 36 via a threaded member 78. The threaded member 78 is fixedly connected to the actuation rod 36 such that when the knob 38 is rotated, the threaded member 78 is rotated together with the actuation rod 36.

The first member 64, i.e. the disc 68 comprise one or more openings 80 and the third member 76 comprise a projection 82.

Returning to FIG. 2, herein the medicament delivery device 2 is illustrated in an initial state with inner plunger rod 34 arranged in an end position towards the distal end portion 10, and the medicament container 20 with medicament components unmixed.

The third member 76 of the locking arrangement 62 is positioned in a blocking position in abutment with the second member 66. Thus, the second member 66 is prevented from being unintentionally actuated. The projection 82 extends through one of the openings in the first member 64 to achieve a releasable engagement between the third and first members 76, 64.

FIG. 4 illustrates a cross section through the embodiments of the medicament delivery device 2 of FIGS. 1-3. In FIG. 4, the medicament delivery device 2 is illustrated in an intermediate state with the inner plunger rod 34 displaced along the longitudinal axis 6 towards the proximal end portion 8 by a user having turned the knob 38, and the medicament container 20 with medicament components mixed in its second space 30.

In this intermediate state, the actuation rod 36 has lost its sliding engagement with the inner plunger rod 34. More specifically, the inner plunger rod 34 has been displaced to an end position towards the proximal end portion 8, and the protrusion 39 of the inner plunger rod 34 has slid out of the slot of the actuation rod 36. Thus, any further rotation of the actuation rod 36 will no longer translate into movement of the inner plunger rod 34 along the longitudinal axis 6.

Compared to the medicament delivery device 2 illustrated in FIG. 2, the knob 38 and the actuation rod 36 have been rotated by a user. Thus, the first piston 24 has been displaced towards the second piston 26, and the resilient projection 42 of the outer plunger rod 32 has engaged with the recess of the inner plunger rod 34. The rotation of the actuation rod 36 has also slid the third member 76 of the locking arrangement 62 along the longitudinal axis 6 and out of the abutment with the second member 66. Moreover, the rotation of the actuation rod has slid the third member 76 along the longitudinal axis 6 and release the releasable engagement with the first member 64, i.e. the projection 82 has been slid out of the opening in the first member 64.

FIG. 5 illustrates a cross section through the embodiments of the medicament delivery device 2 of FIGS. 1-4. In FIG. 5, the medicament delivery device 2 is illustrated after injection of the medicament.

Compared to the intermediate state of the medicament delivery device 2 illustrated in FIG. 4, the proximal end portion 8 of the housing 4 has been pressed against a body of a patient to insert a needle (not shown) into the body, whereupon the cover 12 has been pushed into the housing 4. The button 72 has been pushed to release the second end 54 of the torsion spring 19 from its engagement with the housing 4. Whereupon the plunger 16 and the first and second pistons 24, 26 have been displaced by the torsion spring 19 further into the medicament container 20 injecting the medicament via the needle into the patient. When the medicament delivery device 2 was removed from the body, the cover 12 was pushed out of the housing 4 by a spring 84.

This invention should not be construed as limited to the embodiments set forth herein. A person skilled in the art will realize that different features of the described embodiments may be combined to create embodiments other than those described herein, without departing from the scope of the present invention, as defined by the appended claims. It is also understood by those skilled in the art that the cover 12 is an optional feature, which may be omitted in alternative embodiments. Again, other embodiments may comprise an automatic needle penetration function. In alternative embodiments the releasable engagement between the third and first members 76, 64 may be omitted. Embodiments implemented in a nebuliser, wherein the mixing of two medicament components is required before being administered, via a medicament delivery member comprising a nozzle, as a mist to be inhaled by a patient, are equally foreseen by the skilled person. Although the invention has been described with reference to example embodiments, many different alterations, modifications and the like will become apparent for those skilled in the art. Therefore, it is to be understood that the foregoing is illustrative of various example embodiments and that the invention is defined only the appended claims.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A medicament delivery device comprising:
    a housing;
    an outer plunger rod;
    a torsion spring;
    an actuation rod operatively connected to a user accessible knob, where the actuation rod comprises a slot that is elongated parallel to a longitudinal axis of the housing; and
    an inner plunger rod comprising a protrusion configured to engage the slot and having a threaded engagement with the outer plunger rod,
    wherein user rotation of the knob rotates the actuation rod and displaces the inner plunger rod from a first position to a second position, where the protrusion disengages the slot when the inner plunger rod reaches the second position, and wherein the torsion spring releases stored energy to drive the inner plunger rod and the outer plunger rod proximally along the longitudinal axis relative to the actuation rod.

2. The medicament delivery device of claim 1 further comprising a cover operatively engaged with a spring, where the cover axially slides proximally relative to the housing when pushed against a body of a patient and where removal of the cover from the body causes the spring to push the cover distally such that a portion of the cover extends out beyond a terminal distal end of the housing.

3. The medicament delivery device of claim 1, further comprising a driver that is slidably connected with the outer plunger rod such that the outer plunger rod will to move relative to the driver and along the longitudinal axis.

4. The medicament delivery device of claim 3, the torsion spring being configured to transfer a torque via the drive member to the outer plunger rod.

5. The medicament delivery device of claim 1, further comprising a medicament container having a first piston and a second piston, wherein the outer plunger rod is adapted to engage the inner plunger rod to move proximally in unison with the inner plunger rod when the inner plunger rod is positioned such that the first piston is in contact with the second piston.

6. The medicament delivery device of claim 5, wherein the outer plunger rod comprises a resilient projection adapted to engage a recess in the inner plunger rod when the inner plunger rod is positioned such that the first piston is in contact with the second piston.

7. The medicament delivery device of claim 1, wherein the housing further comprises a threaded inner surface, wherein the outer plunger rod comprises a threaded outer surface that engages the threaded inner surface, and wherein a first end of the torsion spring is connected to the housing and a second end of the torsion spring is connected to the outer plunger rod and is releasably engaged with the housing.

8. The medicament delivery device of claim 1, further comprising a first piston, a second piston, and a medicament container, wherein the actuation rod is adapted to lose its sliding engagement with the inner plunger rod when the inner plunger rod is positioned such that the first piston is in contact with the second piston.

9. An assembly for mixing medicament within a dual chambered cartridge comprising:
a housing;
a container holder configured to accept a dual chambered cartridge having a first piston and a second piston, both pistons being slidable in a proximal direction relative to the container holder;
an inner plunger rod comprising a protrusion, where the inner plunger rod moves axially from a first position to a second position;
an actuation rod slidably positioned within the inner plunger rod, where the actuation rod comprises a slot that is elongated parallel to a longitudinal axis of the housing and is engaged with the protrusion as the inner plunger rod moves from the first position to the second position; and
a knob configured for manual rotation by a user, wherein rotation of the knob rotates the actuation rod to cause the engagement of the slot and protrusion to rotate the inner plunger rod from the first position to the second position, where when the inner plunger rod reaches the second position, the slot and protrusion are disengaged, and
wherein the movement of the inner plunger rod from the first position to the second position moves the first piston relative to the second piston.

10. The assembly of claim 9 further comprises an outer plunger rod surrounding the inner plunger rod and having a first threaded engagement with the housing.

11. The assembly of claim 10, wherein the inner plunger rod has a second threaded engagement with the outer plunger rod.

12. The assembly of claim 10 further comprises a torsion spring having a first end and a second end, where the second end is connected to the housing.

13. The assembly of claim 10, wherein the actuation rod is rotatable with respect to the inner plunger rod when the protrusion is disengaged from the slot.

14. An assembly for expelling a mixed medicament from a dual chambered cartridge comprising:
a housing;
a torsion spring having a first end and a second end, where the second end is connected to the housing;
a container holder configured to accept a dual chambered cartridge having a first piston and a second piston, both pistons being slidable in a proximal direction relative to the container holder;
an outer plunger rod surrounding the inner plunger rod and having a first threaded engagement with the housing;
an inner plunger rod comprising a protrusion, where the inner plunger rod moves axially from a first position to a second position and has a second threaded engagement with the outer plunger rod;
a drive member axially fixed relative to the housing and slidably connected to the outer plunger rod and to the second end of the torsion spring;
an actuation rod slidably positioned within the inner plunger rod, where the actuation rod comprises a slot that is elongated parallel to a longitudinal axis of the housing and is engaged with the protrusion as the inner plunger rod moves from the first position to the second position;
wherein when the torsion spring releases stored energy, both the drive member and the outer plunger rod rotate, causing the outer plunger rod to move axially in a proximal direction relative to the housing;
wherein the outer plunger rod becomes fixed to the inner plunger rod when the inner plunger rod reaches the second position such that the rotation of the outer plunger rod causes the inner plunger rod to move axially in the proximal direction and to slide the first and second pistons such that the mixed medicament is expelled from the dual chambered cartridge.

15. The assembly of claim 14, further comprising a cover operatively engaged with a spring, where the cover axially slides proximally relative to the housing when pushed against a body of a patient and where removal of the cover from the body to causes the spring to push the cover distally such that a portion of the cover extends out beyond a terminal distal end of the housing.

16. The assembly of claim 14, further comprising a lock having a first structure that is releasably positioned with a second structure that secures the torsion spring in an energy-storing position.

17. The assembly of claim 16, wherein the first structure comprises a disc provided with peripheral radial slots and the second structure comprises a protruding part that fits into the radial slots.

18. The assembly of claim 14, the outer plunger rod further comprising a projection and the inner plunger rod further comprising a recess, the projection adapted to engage the recess when the protrusion is disengaged from the slot.

19. The assembly of claim 14, wherein the outer plunger rod comprises a projection adapted to engage a recess in the inner plunger rod when the first piston is in contact with the second piston.

20. The assembly of claim 14, wherein the housing further comprises a threaded inner surface, wherein the outer plunger rod comprises a threaded outer surface that engages the threaded inner surface.

\* \* \* \* \*